(12) United States Patent
Hanke et al.

(10) Patent No.: US 8,326,009 B2
(45) Date of Patent: Dec. 4, 2012

(54) METHOD FOR PRODUCING AN X-RAY IMAGE DURING A MAMMOGRAPHY

(75) Inventors: Wilhelm Hanke, Rückersdorf (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 560 days.

(21) Appl. No.: 12/513,527

(22) PCT Filed: Oct. 15, 2007

(86) PCT No.: PCT/EP2007/060974
§ 371 (c)(1),
(2), (4) Date: May 5, 2009

(87) PCT Pub. No.: WO2008/055760
PCT Pub. Date: May 15, 2008

(65) Prior Publication Data
US 2010/0061614 A1    Mar. 11, 2010

(30) Foreign Application Priority Data
Nov. 9, 2006   (DE) .................... 10 2006 052 874

(51) Int. Cl.
G06K 9/00        (2006.01)
(52) U.S. Cl. .................... 382/128; 378/1; 378/4; 378/5; 378/37; 382/131; 382/132; 382/284

(58) Field of Classification Search .................. 378/1, 4, 378/5, 18, 19, 37; 382/131, 132, 128, 284
See application file for complete search history.

(56) References Cited

U.S. PATENT DOCUMENTS

| | | | |
|---|---|---|---|
| 5,485,501 A | 1/1996 | Aichinger | |
| 6,556,655 B1 | 4/2003 | Chichereau et al. | |
| 7,342,999 B2 * | 3/2008 | Johansson et al. | 378/117 |
| 7,916,915 B2 * | 3/2011 | Gkanatsios et al. | 382/128 |
| 2002/0070365 A1 | 6/2002 | Karellas | |
| 2003/0194050 A1 * | 10/2003 | Eberhard et al. | 378/37 |
| 2004/0234032 A1 | 11/2004 | Nokita | |
| 2005/0195938 A1 | 9/2005 | Zetterlund | |
| 2006/0262904 A1 | 11/2006 | Mertelmeier | |
| 2008/0187095 A1 * | 8/2008 | Boone et al. | 378/37 |

FOREIGN PATENT DOCUMENTS

| | | |
|---|---|---|
| DE | 199 62 281 | 6/2001 |
| WO | WO 00/05677 | 2/2000 |

* cited by examiner

Primary Examiner — Layla Lauchman
Assistant Examiner — Iyabo S Alli
(74) Attorney, Agent, or Firm — Schiff Hardin LLP

(57) ABSTRACT

In a continuous mammography procedure, the breast of a subject is fixed in place in a retention device, and a first x-ray image is generated by irradiating the breast in the retention device. While the breast is still held in the retention device, the first x-ray image is evaluated to define a condition for generating a second x-ray image. The second x-ray image is then generated according to the defined condition, with the breast still in the same position in the retention device.

13 Claims, 1 Drawing Sheet

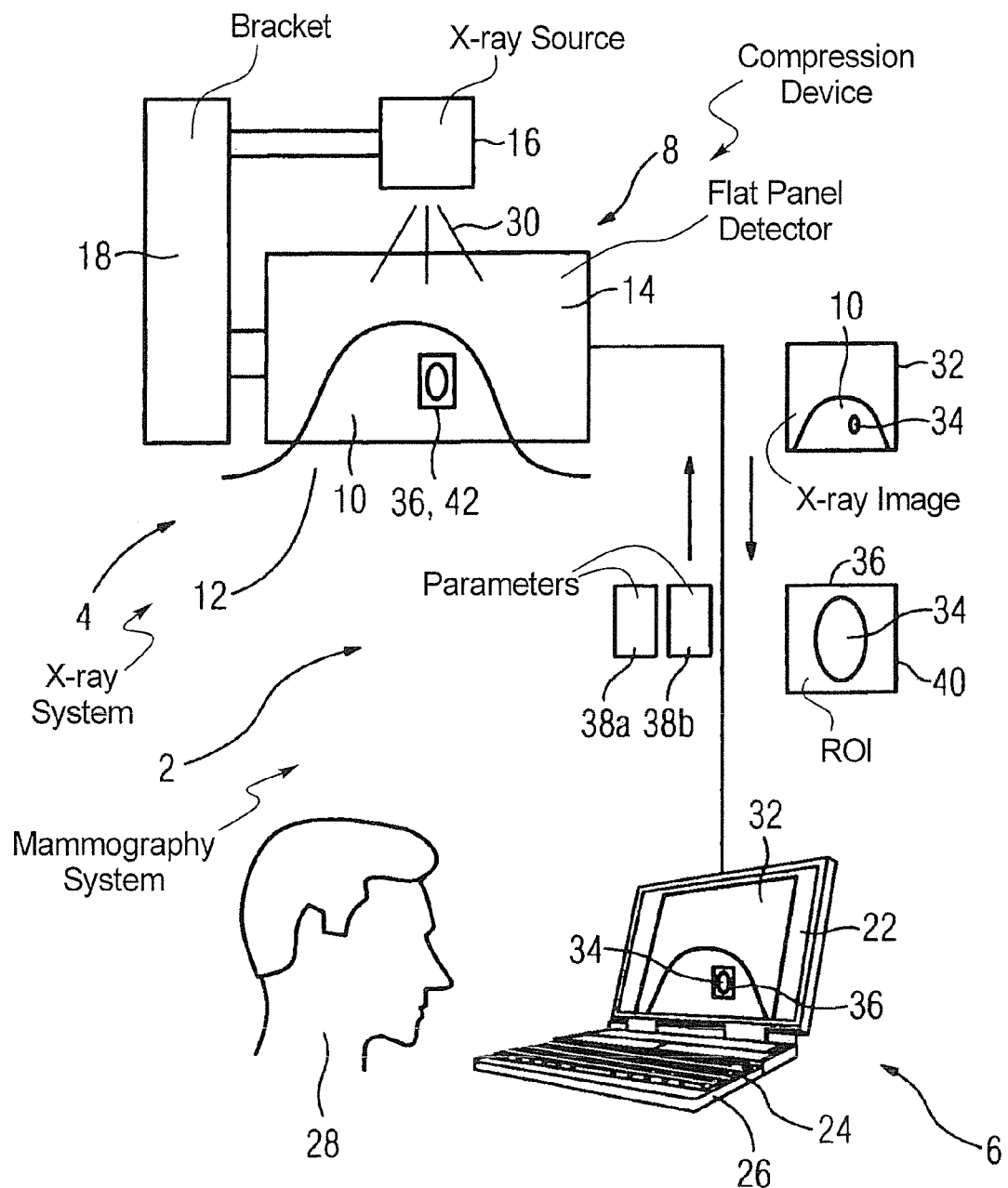

METHOD FOR PRODUCING AN X-RAY IMAGE DURING A MAMMOGRAPHY

BACKGROUND OF THE INVENTION

1. Field of the Invention

The invention concerns a method for generating an x-ray image during a mammogram of a breast, wherein the breast is fixed in a retention device.

2. Description of the Prior Art

Mammography, thus x-ray radioscopy of the breast of a (normally) female patient, has permeated medical practice as an examination method. Mammography today is normally conducted digitally, meaning that the corresponding x-ray images are generated by a digital x-ray radiator (for example a flat panel detector).

In known mammography systems today it is typical to fix or compress the breast in a retention device and to thereby generate a single x-ray exposure with static acquisition parameters. The breast is then released from the compression device again. If in the scope of mammography a second x-ray exposure is required, for example for a biopsy or a detail acquisition for fine diagnosis, the patient or the breast is re-fixed in the compression or retention device.

Normally at least multiple hours, days or weeks occur between two such x-ray exposures. The medical workflow in the scope of the entire mammography is thus slow and laborious. The examination time for the patient is long since said patient must run through the complete x-ray procedure (including fixing of the breast) twice. The patient receives twice the dose of a single exposure due to the two separate x-ray exposures.

SUMMARY OF THE INVENTION

An object of the present invention to provide an improved method for the generation of an x-ray during a mammography procedure.

This object is achieved by a method in accordance with the invention for generation of an x-ray image during a continuous mammographic procedure wherein breast is fixed in the retention device or compression device during the entire procedure. The breast is first radiographed with x-ray radiation to generate a first x-ray image or a first partial exposure or exposure section. According to the invention, while the breast is still fixed in the retention device, the first x-ray image is evaluated to determine a condition for a second application of x-ray radiation, and the breast is radiographed with x-ray radiation according to that condition to generate a second x-ray image or a second partial exposure or exposure section. The condition determines the framework, acquisition parameters, execution, etc. of the second x-ray acquisition.

Since the breast is fixed in the retention device during the entire method, the medical workflow in the mammogram remains significantly accelerated. Two x-ray exposures are created that are matched to one another since, based on the first exposure (namely by evaluation thereof and determination of a corresponding condition), the second exposure is produced according to this condition. The entire examination time of the patient is distinctly shortened since both x-ray exposures are produced in prompt succession, thus in the second or, respectively, minute range. In that the breast is not released from the retention device, the exposure conditions for both x-ray images are exactly alike. The determination of the condition for the second x-ray image is thus simplified on the basis of the first x-ray image.

Digital x-ray detectors are available that do not erase, but rather retain, the charge or image information arising upon the incidence of x-ray radiation upon readout of a corresponding x-ray image (described by the charge or image information) generation of a digital x-ray image. With such detectors it is thus possible to additively acquire additional x-ray radiation in the detector after a first radiation of x-ray radiation and readout of a corresponding x-ray image. In other words, it is possible to continue the exposure of the first x-ray image in order to acquire an additional or modified or expanded x-ray image. In this case the aforementioned first and second x-ray images are thus to be understood in the sense of partial exposures or exposure segments. In the second x-ray image, the image information of the first x-ray image or of the first partial exposure or of the first exposure segments is then retained in addition to the information from the second application of x-ray radiation.

Multiple alternatives exist for the determination of the condition for the second x-ray image.

To determine the condition, the first x-ray image can be automatically evaluated with regard to x-ray exposure parameters and/or x-ray dose. This is possible since, as mentioned above, many boundary conditions—for example acquisition geometry, compression state of the breast etc.—do not change within the short time between first and second x-ray acquisition while the breast remains fixed in the retention device. The evaluation or determination of x-ray acquisition parameters for the second x-ray image thus lead to a second x-ray image that is possibly qualitatively further improved relative to the first x-ray image. Overall a dose reduction for the patient can be achieved with regard to both x-ray images. Due to automatic evaluation, this can be implemented particularly promptly (in contrast to the consideration and finding by a physician) and independent of its momentary availability etc. The time for acquisition of both x-ray images—thus the time during which the patient must remain fixed in the retention device—can thus be reduced to a few minutes or seconds.

An optimal adaptation of the parameters for the sum image made up of first and second partial exposure thus results in particular for the aforementioned method variants with two partial exposures or exposure segments since the parameters required to generate a complete image of optimal image quality can be determined for the second partial exposure from a "preshot" (first partial exposure) obtained for the first partial exposure according to the method.

Alternatively, to determine the condition the first x-ray image can also be automatically evaluated by means of image processing. For example, specified regions in the first x-ray image whose quality is to be improved in the second x-ray image can be determined via corresponding automatic image processing. For example, a particularly interesting region of the x-ray image (ROI, region of interest)—for example a tumor, a suspicious image structure or the like—can also be detected, and thus a second x-ray exposure optimized corresponding to this region of interest can be produced.

In particular, an automatic CAD analysis (Computer Aided Detection/Diagnosis) of the first x-ray image can therefore be conducted as an image processing. CAD systems or algorithms attempt to automatically determine the corresponding medically interesting aspects of the first x-ray image and thus to establish the condition for a corresponding second x-ray image.

Alternatively, to determine the condition the first x-ray image can be displayed to a user and the user establishes the condition. For example, this is reasonable for such cases when a qualified viewer is available in a timely manner or if automatic algorithms arrive at no reasonable evaluation result or a manual inspection of the first x-ray image is desirable anyway.

Various alternatives also exist for the conditions to be defined for the acquisition of the second x-ray image.

An image field altered relative to the first x-ray image can be defined as a condition for the second x-ray image. For example, the altered image field can be distinctly reduced in size relative to the first x-ray image in order to establish a detail of the first x-ray image in the second x-ray image again, in particular with modified acquisition parameters for better visualization. In this case the first x-ray image serves as a rough overview image and the second x-ray image serves as a detail image, for example.

Alternatively, an x-ray dose for the second x-ray image that, for example, ensures its maximum image quality can also be defined as a condition. For example, deficits with regard to the image quality can be uncovered via evaluation of the first x-ray image and the x-ray dose can be accordingly optimized in the second x-ray image. It is thus ensured that a high-quality x-ray image is generated with the second x-ray image in every case via a single fixation of the patient in the retention device. The patient thus avoids enduring the x-ray procedure, in particular compression, without generating a usable x-ray image in the end.

Alternatively, a parameter affecting the beam quality of the x-ray radiation can also be defined as a condition for the second x-ray exposure. For example, with regard to the beam quality a corresponding acceleration voltage or a specific anode/filter combination can be selected which is optimal for the intended depiction of specific structures. For example, if a tumor or a micro-calcification is diagnosed in the first x-ray image, the x-ray parameters can be correspondingly selected for optimal depiction of a tumor or a micro-calcification. It is thus ensured that the detail of interest is presented in the best image quality at least in the second x-ray image.

The x-ray images can be generated by an x-ray detector with variable resolution. The resolution for the second x-ray exposure is then determined as a condition. For example, in the second x-ray exposure the detector is to be switched to maximum resolution (for example for a small image field) while this was only operated with standard resolution to generate an overview image to conduct the first x-ray acquisition.

A fast solid state detector with high image rate can be used to generate the x-ray images. Such a digital x-ray radiation detector allows the method to be conducted in a time frame of under one minute, for example, which is advantageous for the patient since said patient is painfully or, respectively, uncomfortably clamped in the retention device during the entire time.

In the framework of the method, first and second x-ray image can be stored and displayed separately from one another. For example, this allows the observer a known separation of overview and detail exposure in a conventional manner in order to be able to view and assess both in parallel but simultaneously, for example.

Alternatively, however, the first and second x-ray images can be fused into a combination image and the sum image can be stored and displayed. For example, both a rough overview and a specific detail can be shown in particularly high contrast or with high resolution in a single x-ray image via the fusing into a sum image. The particularly emphasized detail thus appears in its direct context or, respectively, the immediate surroundings (represented by the remainder of the first x-ray image) in the single sum image.

In contrast to the aforementioned alternatives of two partial exposures adding up the x-ray dose in the x-ray detector, here two actual separate x-ray images are thus generated; the image content of the x-ray detector is thus deleted between the two x-ray images and first and second x-ray image are actually only fused together via calculation later.

BRIEF DESCRIPTION OF THE DRAWING

The single FIGURE schematically illustrates a mammography system for implementing a mammographic procedure on a patient in accordance with the present invention.

DESCRIPTION OF THE PREFERRED EMBODIMENTS

The FIGURE shows a mammography system 2 having an x-ray system 4 and an acquisition workstation 6. The x-ray system 4 has a bracket 8 or compression device for fixing a breast 10 of a patient 12 (symbolically shown). The bracket 8 carries an x-ray flat panel detector 14 and a compression plate (not shown in FIG. 1) interacting with the flat panel detector.

The flat panel detector 14 is attached on a bearing device 18 together with an x-ray source 16. The x-ray system 4 is connected via a data line 20 with the workstation 6, which essentially comprises a monitor 22, a keyboard 24 and a computer 26.

A physician would like to now conduct a mammography of the patient 12. For this he brings the breast 10 of said patient 12 into the bracket 8 and starts the x-ray source 16 via the workstation 6, which x-ray source 16 emits x-ray radiation 30 through the breast 10 towards the flat panel detector 14. This supplies a first x-ray image 32 to the workstation 6, which graphically renders the entire imaging region, thus the area of the flat panel detector 14 shown in FIG. 1. An image of the breast 10 with a suspicious region 34 is recognizable in the x-ray image 32. The x-ray image 32 is displayed to the physician on the monitor 22.

In a first alternative, the physician 28 now evaluates the x-ray image 32 and identifies an imaged region 34 as being of particular interest to him. He therefore manually establishes an ROI 36 (region of interest) in the x-ray image 32 which essentially contains the region 34.

Alternatively, a computer program running on the computer 26 analyzes the x-ray image 32 and automatically identifies the imaged region 34 as a subject of interest which is to be imaged more precisely. The computer 26 therefore defines the ROI 36 in the x-ray image 32.

The computer 26 communicates two parameters 38a,b (in reality this can clearly be more) to the x-ray system 4 via the data line 20, which two parameters 38a,b represent the acquisition conditions for a further emission of x-rays 30. The parameter 38a namely defines the geometry of the ROI 36 to the effect that an image field 42 is set by aperture diaphragms (not shown) in front of the x-ray source 16 so that only the ROI 36 is exposed with x-ray radiation 30 on the flat panel detector 14. In contrast to this, the parameter 38b switches the internal pixel resolution of the flat panel detector 14 to be distinctly finer relative to the x-ray exposure 32 so that the ROI 36 with the region 34 is shown with higher detail in the x-ray image 40.

The breast 10 can now be released from the bracket 8.

The x-ray image 40 is likewise transferred from the x-ray system 4 to the workstation 6 and there is fused by the computer 26 with the first x-ray image 32 such that the ROI 36 according to the image information from the x-ray image 40 with distinctly increased detail resolution is overlaid in the remaining x-ray image 32. Via a corresponding operation of the workstation 6, the physician 28 can now zoom the region of interest (namely the ROI 36) to the full size of the screen 22 in order to view the region 34 in accurate detail.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating x-ray images in a mammographic procedure, comprising the steps of:
    holding a breast to be imaged in a fixed position in a mechanical retention device;
    irradiating the breast in the retention device with x-rays and generating first image information in a radiation detector from x-rays attenuated by the breast in the retention device that are detected by the radiation detector, and generating a first x-ray image of the breast in the retention device from said first image information;
    while the breast is still in said fixed position in said retention device, evaluating said first x-ray image to identify a condition for generating a second x-ray image of the breast;
    erasing said first image information from said radiation detector; and
    with the breast still in said fixed position in said retention device, again irradiating the breast with x-rays, according to the condition defined by evaluation of said first x-ray image, and generating second x-ray image information of the breast from x-rays attenuated by the breast in said fixed position that are detected by the radiation detector, and generating a second x-ray image of the breast in the retention device from said second image information.

2. A method as claimed in claim 1 comprising generating said first x-ray image as a first partial exposure of the breast and generating said second x-ray image as a second partial exposure of the breast, and generating a single x-ray image of the breast as a sum of said first and second x-ray images.

3. A method as claimed in claim 1 comprising automatically, non-manually evaluating said first x-ray image in a processor to define said condition.

4. A method as claimed in claim 3 comprising automatically evaluating said first x-ray image in said processor to define said condition as a condition selected from the group consisting of acquisition parameters for operating an x-ray source to generate said second x-ray image, and a radiation dose of said x-rays for generating said second x-ray image.

5. A method as claimed in claim 3 comprising defining said condition in said processor by executing a CAD analysis of said first x-ray image.

6. A method as claimed in claim 1 comprising displaying said first x-ray image as a visual representation at a display device, and defining said condition by manual evaluation of said first x-ray image displayed at said display device.

7. A method as claimed in claim 1 wherein said first x-ray image contains an image field, and comprising defining said condition as a defined modification of said image field.

8. A method as claimed in claim 1 comprising irradiating the breast in said fixed position with an x-ray dose to generate said first x-ray image, and comprising defining said condition as a modification of said x-ray dose for generating said second x-ray image.

9. A method as claimed in claim 1 comprising irradiating said breast in said fixed position with x-rays from an x-ray source operated according to at least one parameter that effects beam quality of said x-ray radiation, and defining said condition as a modification of said at least one parameter that effects said beam quality of said x-ray radiation.

10. A method as claimed in claim 1 comprising generating said first x-ray image of the breast by detecting said x-rays attenuated by the breast with an x-ray detector having a variable resolution, and comprising defining said condition as a modification of said resolution for generating said second x-ray image.

11. A method as claimed in claim 1 comprising detecting said x-rays to generate each of said first and second x-ray images using a flat solid state x-ray detector.

12. A method as claimed in claim 1 comprising separately storing and displaying each of said first and second x-ray images.

13. A method as claimed in claim 1 comprising fusing said first and second x-ray images to form a fused image of said breast, and storing and displaying said fused image.

* * * * *